United States Patent [19]

Maul et al.

[11] Patent Number: 4,952,719

[45] Date of Patent: Aug. 28, 1990

[54] PROCESS FOR THE PREPARATION OF HALO AROMATIC COMPOUNDS

[75] Inventors: James J. Maul, Grand Island; David Y. Tang, East Amherst, both of N.Y.

[73] Assignee: Occidental Chemical Corporation, Niagara Falls, N.Y.

[21] Appl. No.: 303,862

[22] Filed: Jan. 27, 1989

Related U.S. Application Data

[63] Continuation of Ser. No. 825,505, Feb. 3, 1986, abandoned, which is a continuation-in-part of Ser. No. 660,765, Oct. 15, 1984, Pat. No. 4,590,315.

[51] Int. Cl.$^5$ ............................................. C07C 121/52
[52] U.S. Cl. .................................................... 558/425
[58] Field of Search ........................................ 558/425

[56] References Cited

U.S. PATENT DOCUMENTS

| | | | |
|---|---|---|---|
| 4,209,457 | 6/1980 | Fuller | 260/465 G |
| 4,225,534 | 9/1980 | Yoshikawa | 260/460 G |
| 4,351,777 | 9/1982 | Ramanadin et al. | 260/465 G |
| 4,388,472 | 6/1983 | Cartwright et al. | 560/21 |
| 4,582,948 | 4/1986 | Tang et al. | 568/938 |

*Primary Examiner*—Robert Gerstl
*Attorney, Agent, or Firm*—James F. Tao; Arthur S. Cookfair

[57] ABSTRACT

A process for the preparation of 3-chloro-4,5-difluorobenzonitrile comprising the steps of (a) reacting an alkali metal fluoride with 4-chloro-3,5-dinitrobenzonitrile to form a 4-fluoro-3,5-dinitrobenzonitrile product;

(b) chlorodenitrating the 4-fluoro product of step (a) to form the corresponding 3,5-dichloro-4-fluorobenzonitrile compound; and (c) reacting the 3,5-dichloro-4-fluorobenzonitrile compound prepared in step (b) with an alkali metal fluoride to form 3-chloro-4,5-difluorobenzonitrile.

9 Claims, No Drawings

PROCESS FOR THE PREPARATION OF HALO AROMATIC COMPOUNDS

REFERENCE TO PRIOR APPLICATION

This is a continuation of application Ser. No. 825,505, filed Feb. 3, 1986, now abandoned, which is a continuation-in-part of application Ser. No. 660,765, filed Oct. 15, 1984 now U.S. Pat. No. 4,590,315.

BACKGROUND OF THE INVENTION

This invention relates to a method for the preparation of 3-chloro-4,5-difluorobenzonitrile. The compounds prepared in accordance with the invention are useful as intermediates in the preparation of various chemical products, in particular, in the preparation of substituted diphenyl ethers having herbicidal properties.

A prior art method for preparation of the compound, 3-chloro-4,5-difluorobenzotrifluoride and the use thereof as an intermediate in the manufacture of herbicidal diphenyl ethers is disclosed in U.S. Pat. No. 4,388,472. The preparation disclosed therein involves the steps of (1) reacting chlorine with p-trifluoromethylaniline in glacial acetic acid to form 2,6-dichloro-4-trifluoromethylaniline; (2) diazotization of the latter; (3) reaction of the diazo product with cuprous chloride in concentrated hydrochloric acid to form 3,4,5-trichlorobenzotrifluoride and (4) reaction with KF to form 3-chloro-4,5-difluorobenzotrifluoride. The patent further discloses the preparation of 3,5-dichloro-4-fluorobenzotrifluoride by diazotization of 2,6-dichloro-4-trifluoromethylaniline followed by reaction with sodium fluoroborate and decomposition of the product. Such methods, although useful for laboratory preparations are less suitable for commercial scale preparations. The starting material, p-trifluoromethylaniline, is expensive. Furthermore, the diazotization reaction is expensive and not readily adaptable to commercial scale. Furthermore, step 4 of the prior art route of synthesis, that is, the reaction of KF with 3,4,5-trichlorobenzotrifluoride, leads to the formation of an isomeric mixture of 3-chloro-4,5-difluorobenzotrifluoride and 4-chloro-3,5-difluorobenzotrifluoride, and thus requires additional separation procedures. For similar considerations, the prior art synthetic route utilizing diazotization and halogenation in a manner similar to that detailed above for the preparation of 3-chloro-3,4-difluorobenzotrifluoride would also be unsatisfactory, if applied to the analogous commercial scale preparation of 3-chloro-4,5-difluorobenzonitrile.

Halogen exchange reactions wherein an alkali metal fluoride, such as KF, is reacted with a chloro-aromatic compound to form the corresponding fluoro-aromatic compound are well-known in the prior art. A typical example of such reactions is that described above wherein KF is reacted with 3,4,5-trichlorobenzotrifluoride to form 3-chloro-4,5-difluorobenzotrifluoride (U.S. Pat. No. 4,388,472).

Chlorodenitration reactions wherein a chlorinating agent is reacted with a nitro-aromatic compound to form the corresponding chloro-aromatic compound, are known in the prior art. See, for example, U.S. Pat. No. 4,470,930, which discloses the vapor phase chlorodenitration of nitro-benzonitriles to form the corresponding chloro-benzonitriles. The liquid phase chlorodenitration of 2-nitrobenzonitriles to form the corresponding 2-chlorobenzonitriles is disclosed in U.S. Pat. No. 4,225,534.

The compound prepared in accordance with this invention, that is 3-chloro-4,5-difluorobenzonitrile is a useful intermediate for the preparation of herbicidal diphenyl ethers, for example, of the type disclosed in European Patent Application Publication No. 0 23 392, and U.S. Pat. No. 4,388,472.

Accordingly, it is an object of this invention to provide a synthetic route for the preparation of high purity, substantially isomer-free 3-chloro-4,5-difluorobenzonitrile that is well suited for both laboratory and commercial scale preparations. It is a further object to provide a method for the preparation of novel benzonitrile compounds.

SUMMARY OF THE INVENTION

It has now been found that 3-chloro-4,5-difluorobenzonitrile may be prepared by a process comprising the steps of (a) reacting an alkali metal fluoride with 4-chloro-3,5-dinitrobenzonitrile to form 4-fluoro-3,5-dinitrobenzonitrile;

(b) chlorodenitrating the 4-fluoro product of step (a) to form 3,5-dichloro-4-fluorobenzonitrile;

(c) reacting the 3,5-dichloro-4-fluorobenzonitrile with an alkali metal fluoride to form the corresponding 3-chloro-4,5-difluorobenzonitrile.

The sequence of steps that constitute the process of this invention may be illustrated by the following chemical equation

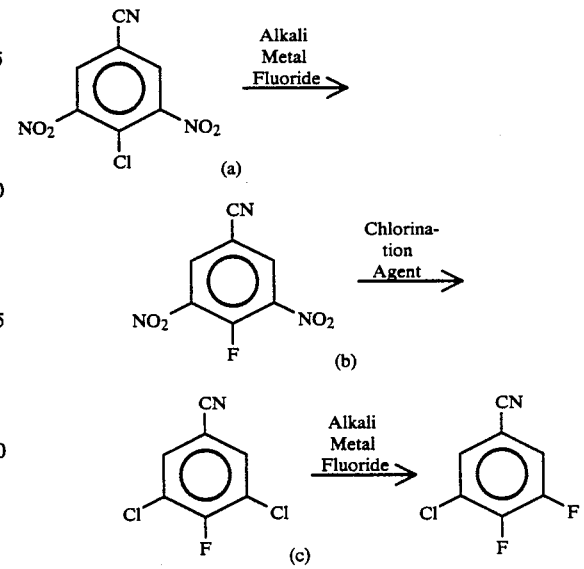

In the stepwise process detailed above, fluorination steps (a) and (c) are preferably carried out in the liquid phase. The preferred alkali metal fluoride to be employed as a fluorinating agent is potassium fluoride. Either or both of the fluorination steps (a) and (c) may be carried out near or in the presence of a solvent. It is preferred to carry out both step (a) and step (c) in the presence of a solvent. Suitable solvents that may be employed in either step (a) or step (c) include, for example, N-methyl-2-pyrrolidone, sulfolane, N,N-dimethylformamide, N,N-dimethylacetamide, N,N-diethylformamide, dimethylsulfoxide, diethylsulfoxide, dipropylsulfoxide, dioctylsulfoxide, dimethylsulfone, diethylsulfone, diphenylsulfone, and the like, and mixtures thereof. In step (a), a lower boiling solvent, such as acetonitrile, may be employed.

When step (a) is carried out neat under atmospheric conditions, the melting point of the 4-chloro-3,5-dinitrobenzonitrile reactant (140.5° C.) dictates the use of a temperature that results in the formation of viscous by-products which inhibit mixing and tend to lower the yields. It has been found that the yield can be substantially improved through the use of efficient stirring or mixing. Furthermore, it has been found that the use of a solvent, such as acetonitrile, permits the use of lower temperatures and results in improved yields.

The fluorination reactions are typically carried out at a temperature of from about 50° to about 300° Celsius under atmospheric or superatmospheric conditions. It is preferred to carry out step (a) at a temperature in the range of about 75° to about 155° Celsius (about 140.5° to about 155° Celsius if the reaction is run neat). Step (c) is preferably carried out at a temperature of about 170° to about 270° Celsius. When the fluorination is carried out at atmospheric pressure, the selection of a solvent may depend, in part, on the temperature to be employed. Thus, for example, since it is preferred to carry out step (c) at a higher temperature, such as about 200° to about 270° Celsius, a higher boiling solvent such as sulfolane may be selected while a lower boiling solvent such as N,N-dimethylformamide or acetonitrile may be appropriate for step (a).

It is preferred to carry out the fluorination steps using a stoichiometric excess of alkali metal fluoride, preferably in a molar ratio of between about 1:1 to about 5:1 of alkali metal fluoride: organic reactant.

The fluorination reaction of steps (a) and (d) proceed readily without the aid of a catalyst. However, a catalyst may be employed effectively to accelerate the reaction. Preferred catalysts are phase transfer catalysts such as tetraphenylphosphonium chloride, hexadecyltributylphosphonium bromide, tetramethylphosphonium chloride, tetramethylammonium chloride, tetradecyltrimethylammonium bromide and the like. Furthermore, such fluorination reactions, involving aromatic compounds, such as chloro-benzonitriles, chloro-benzotrifluorides, and the like, may be facilitated by including a catalytic amount of cesium fluoride with the potassium fluoride reactant.

The chlorodenitration step (b) may be carried out in either the vapor phase or the liquid phase and over a wide range of temperatures, for example, from about 50° to about 500° Celsius. In the liquid phase, the reaction may be carried out neat or in the presence of a solvent. Generally, the liquid phase reaction will be carried out at a temperature of from about 120° to about 250° Celsius under atmospheric pressure. Higher temperatures may be employed under autogenous pressure. Preferably, the chlorodenitration reaction of step (b) is carried out under vapor phase conditions at a temperature of about 250° to about 450° and most preferably about 290° to about 410° Celsius. Various chlorinating agents, such as, PCl$_5$, SOCl$_2$, HCl, Cl$_2$ and the like may be employed, the preferred being Cl$_2$.

In another aspect, this invention relates to the preparation of novel benzonitrile compounds. In particular, the following novel compounds are prepared: 4-fluoro-3,5-dinitrobenzonitrile, the product of step (a), above; 3,5-dichloro-4-fluorobenzonitrile, the product of step (b), above; and 3-chloro-4,5-difluorobenzonitrile, the product of step (c), above. These halo-substituted benzonitriles are useful intermediates for the preparation of various chemical products, especially herbicidal diphenyl ethers.

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1—PREPARATION OF 4-FLUORO-3,5-DINITROBENZONITRILE

A mixture of 7.0 parts of anhydrous potassium fluoride and 5.0 parts of 4-chloro-3,5-dinitrobenzonitrile was heated and maintained at about 150° C., with stirring, for a period of about 6 hours, under a positive pressure of nitrogen. The reaction mixture, a viscous, dark brown liquid was filtered and washed with methylene chloride. Analysis of the filtrate by gas chromatographic techniques indicated a 69% conversion and a 5% yield of 4-fluoro-3,5-dinitrobenzonitrile.

EXAMPLE 2—PREPARATION OF 3-CHLORO-4,5-DIFLUOROBENZONITRILE

The compound 3-chloro-4,5-difluorobenzonitrile is prepared in the following manner:

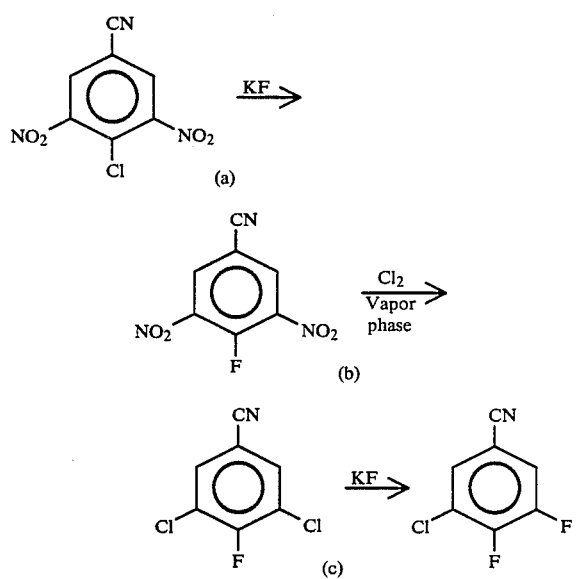

(a) Preparation of 4-fluoro-3,5-dinitrobenzonitrile. A solution of 35 parts of 4-chloro-3,5-dinitrobenonitrile and 13.9 parts of potassium fluoride in 31.94 parts of acetonitrile, was heated to reflux (83° C.) and maintained thereat for about 83 hours. The reaction product was a red liquid. Analysis by gas chromatographic techniques indicated a 100% conversion and 72% yield of 4-fluoro-3,5-dinitrobenzonitrile.

(b) Preparation of 3,5-dichloro-4-fluorobenzonitrile. During a 10-hour period a solution of 216 parts of 4-fluoro-3,5-dinitrobenzonitrile (prepared as in step (a), above) in 1500 parts of carbon tetrachloride, is vaporized by passing through a tubular nickel reactor maintained at about 350° C. and the vapors passed through a second nickel tubular reactor, maintained at about 350°

C., and mixed therein with a stream of chlorine at a molar ratio of $Cl_2$:4-fluoro-3,5-dinitrobenzonitrile of about 6.0. The exiting vapors are collected, condensed and the condensate treated with $MgSO_4$. The desired product, 3,5-dichloro-4-fluorobenzonitrile is isolated by vacuum distillation.

(c) Preparation of 3-chloro-4,5-difluorobenzonitrile. A mixture of 55 parts of anhydrous potassium fluoride and 37 parts of 3,5-dichloro-4-fluorobenzonitrile in 300 parts of sulfolane is heated and maintained, with stirring, at about 250° C. while product vapors are removed through a distillation column to form a condensate containing the desired product, 3-chloro-4,5-difluorobenzonitrile.

The product -chloro-4,5-difluorobenzonitrile, prepared for example as set forth in Example 2, above, is a useful intermediate for the preparation of various end products especially for the preparation of diphenyl ether herbicides. Thus, for example, this compound may be further reacted with the potassium salt of methyl-5-hydroxy-2-nitrobenzoate in a solvent such as N-methyl-2-pyrrolidone at a temperature of about 120° to 180° Celsius to form methyl-5-(2-chloro-4-cyano-6-fluorophenoxy)-2-nitro-benzoate. The ester may be hydrolyzed in a conventional manner to the corresponding carboxylic acid.

What is claimed is:

1. A process for the preparation of 3-chloro-4,5-difluoro-benzonitrile which comprises the steps of
(a) reacting an alkali metal fluoride with 4-chloro-3,5-dinitrobenzonitrile at a temperature of from about 50° to about 300° Celsius to form 4-fluoro-3,5-dinitrobenzonitrile;
(b) chlorodenitrating the 4-fluoro-e,5-dinitro product of step (a) to form 3,5-dichloro-4-fluorobenzonitrile; and
(c) reacting the 3,5-dichloro-4-fluorobenzonitrile compound prepared in step (b) at a temperature of from about 50° to about 300° Celsius with an alkali metal fluoride to form 3-chloro-4,5-difluorobenzonitrile.

2. A process according to claim 1, wherein the alkali metal fluoride of steps (a) and (b) is potassium fluoride.

3. A process according to claim 1, wherein the reactions of steps (a) and (c) are carried out neat at a temperature of 140.5° to about 155° Celsius for the reaction of step (a) and about 170° to about 270° Celsius for the reaction of step (c).

4. A process according to claim 1, wherein the reactions of steps (a) and (c) are carried out in the presence of a solvent at a temperature of about 75° to about 155° Celsius for the reaction of step (a) and about 170° to about 270° Celsius for the reaction of step (c).

5. A process according to claim 1, wherein the reaction of step (a) is carried out neat at a temperature of about 75° to about 155° Celsius in the presence of a solvent and the reaction of step (c) is carried out neat at a temperature of about 170° to about 270° Celsius.

6. A process according to claim 1, wherein the reaction of step (a) is carried out neat at a temperature of about 140.5° to about 155° Celsius in the presence of a solvent and the reaction of step (c) is carried out neat at a temperature of about 170° to about 270° Celsius.

7. A process according to claim 1, wherein the chlorodenitration reaction of step (b) is carried out in the vapor phase at a temperature of about 250° to about 450° Celsius.

8. A process according to claim 7, wherein the chlorodenitration reaction of step (b) is carried out in the vapor phase by reacting $Cl_2$ with 4-fluoro-3,5-dinitrobenzonitrile at a temperature of about 290° to about 410° Celsius.

9. A process for the preparation of 3-chloro-4,5-difluorobenzonitrile which comprises reacting 3,5-dichloro-4-fluoro-benzonitrile with an alkali metal fluoride at a temperature of from about 50° to about 300° Celsius.

* * * * *